US005377496A

United States Patent [19]
Otto et al.

[11] Patent Number: 5,377,496
[45] Date of Patent: Jan. 3, 1995

[54] REFRIGERATION SYSTEM WITH INSTALLED ACID CONTAMINATION INDICATOR

[75] Inventors: Nancy M. Otto, Clay; Warren R. Clough, Cicero; Henry B. Balduzzi, Liverpool, all of N.Y.

[73] Assignee: Carrier Corporation, Syracuse, N.Y.

[21] Appl. No.: 131,584

[22] Filed: Oct. 5, 1993

[51] Int. Cl.$^6$ ............................................. G01K 13/00
[52] U.S. Cl. ........................................ 62/129; 116/206; 436/61
[58] Field of Search ................... 62/129, 125; 116/206; 436/61

[56] References Cited

U.S. PATENT DOCUMENTS

| | | | |
|---|---|---|---|
| 3,084,658 | 4/1963 | Schell | 116/206 |
| 4,923,806 | 5/1990 | Klowdowski | 436/39 |
| 5,071,768 | 12/1991 | Klowdowski | 436/39 |
| 5,127,433 | 7/1992 | Argyle et al. | 62/129 X |

FOREIGN PATENT DOCUMENTS 2353972  4/1975  Germany ................. 62/125

*Primary Examiner*—William E. Wayner

[57] ABSTRACT

An improved vapor compression refrigeration system that has an indicator for detecting the presence of acid contamination in the refrigerant contained in the system. The indicator is permanently or semipermanently installed so that continuous monitoring of the refrigerant for acid is possible. The indicator is located in a portion of the system where the refrigerant is always in a gaseous state. In a preferred embodiment, the indicator is located in a bypass line between the suction and the discharge of the system compressor. The indicator preferably shows the presence of acid by a color change, visible from a point external to the indicator, in an indicator bed in the indicator. The color change may be either permanent or the indicator bed may return to its original color when the acid contamination is no longer present in the refrigerant.

10 Claims, 2 Drawing Sheets

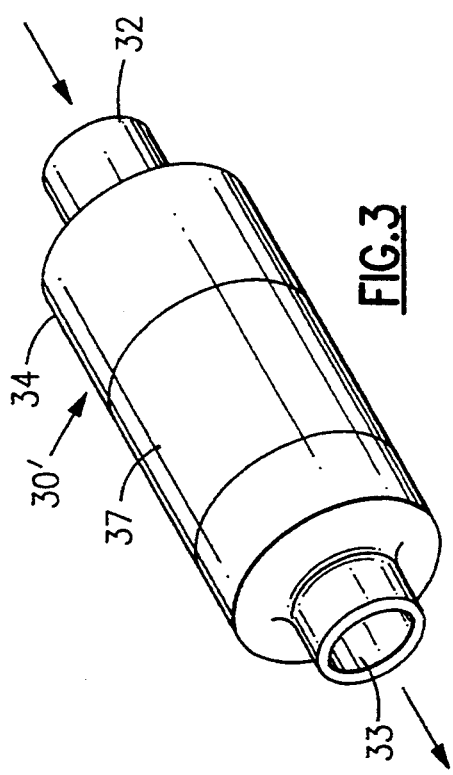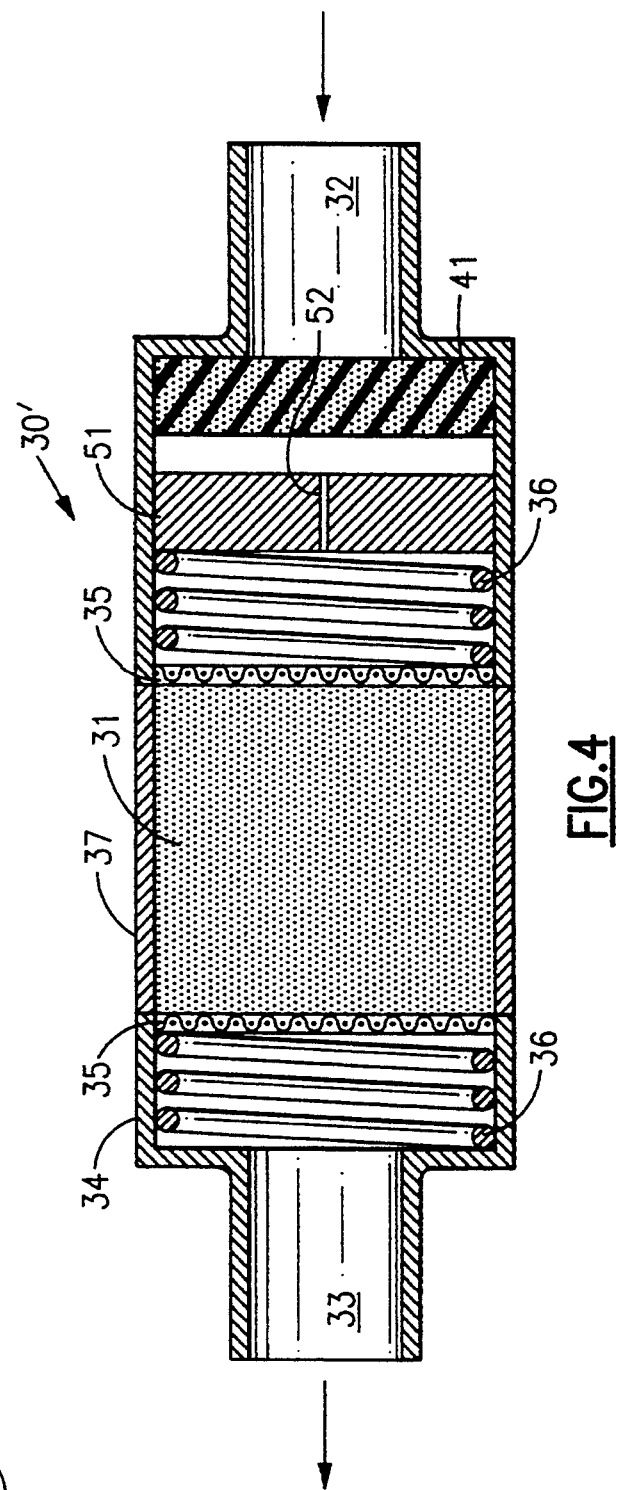

REFRIGERATION SYSTEM WITH INSTALLED ACID CONTAMINATION INDICATOR

BACKGROUND OF THE INVENTION

This invention relates generally to closed loop vapor compression refrigeration systems. In particular, the invention relates to such a system that has an installed indicator to show the presence of acid contamination in the refrigerant contained in the system.

Vapor compression refrigeration systems are used both to cool and heat enclosed spaces. Typical examples of such systems are refrigerators and air conditioning, including heat pump, systems. The refrigerant in a vapor compression refrigeration system may contain acid contaminants. When a refrigerant is subjected to excessive temperatures, such as in an overheating compressor, it may decompose chemically. Commonly, one or more types of acid are found among the decomposition products, regardless of the type of refrigerant. The decomposition products of oil, varnish, insulation, gaskets and adhesives may also include acids. Not only can acids damage system components, their presence in the refrigerant can indicate component failure or imminent failure.

To assure efficient system operation as well as to detect and prevent damage, it is desirable to have a capability to determine the presence of acid contamination and, if present, remove the acid from the system.

U.S. Pat. No. 4,923,806, issued 8 May 1990 to Klowdowski, describes and claims an invention having the same assignee as the present invention. The '806 patent describes a refrigerant testing apparatus that includes a testing tube that is capable of detecting the presence and concentration of inorganic acid as well as water vapor in a stream of refrigerant vapor passing through the tube. The '806 testing apparatus also includes a testing tube holder having provisions to place the testing tube in flow communication with the refrigerant in a refrigeration system. The testing apparatus, marketed by the assignee as the TOTALTEST ® refrigerant testing system, has enjoyed wide acceptance and commercial success.

Another patent, U.S. Pat. No. 5,071,768, issued 10 Dec. 1991 to Klowdowski describes and claims an invention having the same assignee as the present invention. The '768 patent describes another refrigerant testing tube having a different configuration than the '806 tube and that is not only capable of detecting the presence and concentration of both water vapor and inorganic acid in a refrigerant vapor stream but also can detect the presence of other refrigerant contaminants as well.

Both of the patents cited above describe apparatus that are separate from a refrigeration system. The apparatus must be connected to the system specifically to perform a test for refrigerant contamination and then disconnected from the system at the completion of the test. Apparatus of this type can provide useful information but do not allow for continuous monitoring of a system for contamination.

What is needed is a refrigeration system having an acid indicator that is permanently or semipermanently mounted in the system so that the refrigerant in the system can be continually monitored without removing refrigerant from the system.

SUMMARY OF THE INVENTION

The present invention is an improved vapor compression refrigeration system that has an installed indicator to show whether the refrigerant in the system is contaminated with acid. The indicator may be installed at any location in the system where the refrigerant is always in the gaseous phase. In a preferred embodiment the indicator is located in a bypass line around the system compressor.

The indicator is of the chemical type. The indicator chemical is situated where it can come in contact with the system refrigerant. Any acid present in the refrigerant will cause a visible color change in the indicator. In one embodiment of the invention, the composition of the indicator chemical is such that the chemical will undergo a permanent color change when once contacted by acid. In another embodiment of the invention, the composition of the indicator chemical is such that if, after a color change due to the presence of acid, the acid contamination is removed, then the indicator chemical will "regenerate" or return to its original color.

BRIEF DESCRIPTION OF THE DRAWINGS

The accompanying drawings form a part of the specification. Throughout the drawings, like reference numbers identify like elements.

FIG. 3 is an isometric view of one embodiment of the indicator of the present invention.

FIG. 4 is a sectioned elevation view of one embodiment of the indicator of the present invention.

DESCRIPTION OF THE PREFERRED EMBODIMENTS

Figure 1:
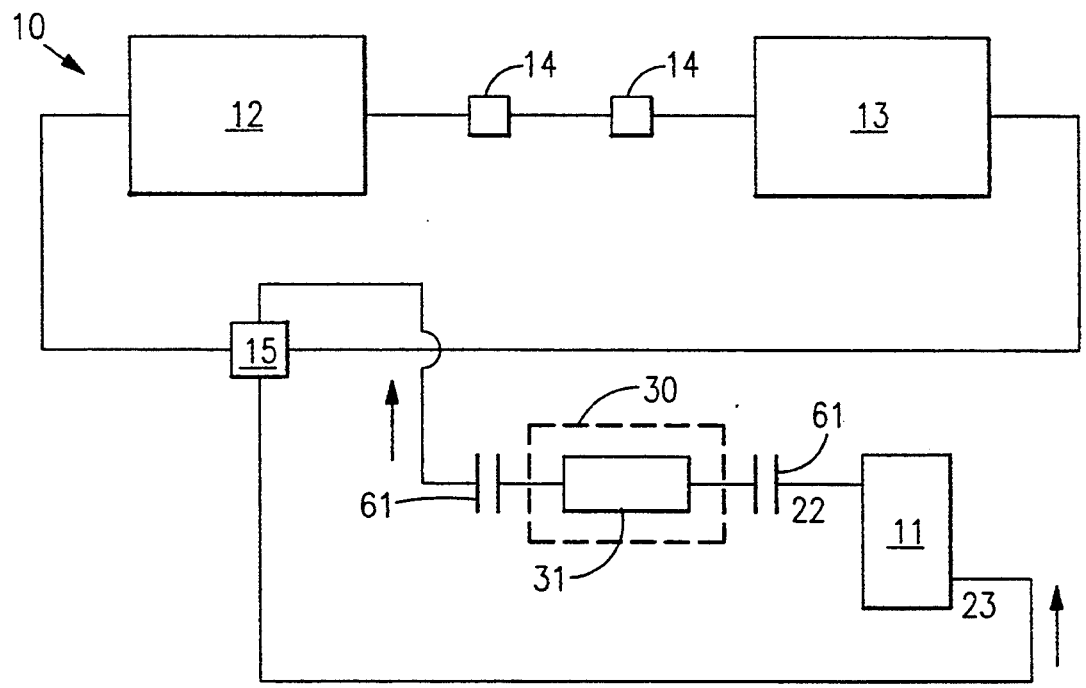
FIG. 1 is a schematic diagram of one embodiment of the present invention.

FIG. 1 shows schematically one embodiment of the present invention. System 10 is a reversible closed loop vapor compression refrigeration system used for air conditioning commonly referred to in the industry as a heat pump. With reversing valve 15 in one of its two positions, refrigerant flows from discharge 22 of compressor 11, through reversing valve 15, heat exchanger 12, first expansion device 14, second expansion device 14, heat exchanger 13, through reversing valve 15 and to suction 23 of compressor 11. With reversing valve 15 in the second of its two positions, the refrigerant flow between compressor 11 and valve 15 remain the same but the flow in the remainder of the loop reverses. Expansion devices 14 are each an apparatus or a combination of apparatus that restrict the flow of refrigerant in one flow direction and offer little or no resistance to flow in the other direction. Devices 14 are installed in the refrigerant flow loop so that each restricts the flow when the flow direction is such that the device is upstream of the heat exchanger to which it is nearest. Whichever of heat exchangers 12 and 13 is in upstream flow relationship with the other heat exchanger functions as a condenser and the downstream heat exchanger functions as an evaporator.

Contaminant indicator 30, containing indicator bed 31, is located immediately downstream of discharge 22 of compressor 11. Indicator 30 is installed in the refrigerant flow loop by means of fittings 61. Fitting 61 may be either of a permanent type or one that would allow easy removal and reinstallation of indicator 30 in the loop.

Figure 2:
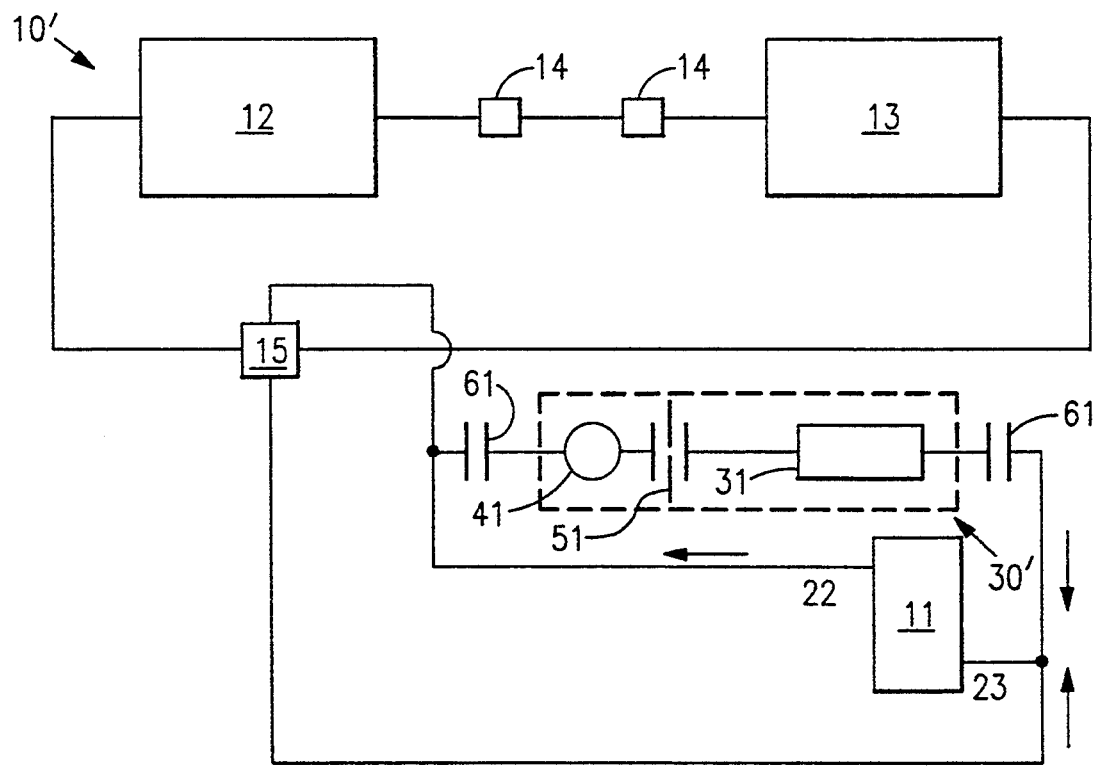
FIG. 2 is a schematic diagram of another embodiment of the present invention.

FIG. 2 shows schematically another embodiment of the present invention. System 10' is also a reversible closed loop refrigeration system. Here, however, contaminant indicator 30' is not located in the main refrigerant flow path but rather in a flow path that carries refrigerant from discharge 22, through indicator 30' then to suction 23. Restrictor 51 limits refrigerant flow through this bypass line and thus through indicator 30'. Filter 41 minimizes the possibility that loose particles in the refrigerant will clog restrictor 51.

Although FIGS. 1 and 2 depict heat pump type refrigeration systems adapted for air conditioning use, one skilled in the art will readily appreciate that the present invention extends to refrigeration systems that do not have reversing valves. In such a system, heat exchanger 12 is either a condenser or an evaporator and heat exchanger 13 is an evaporator, if heat exchanger 12 is a condenser, or a condenser if heat exchanger 13 is an evaporator. In a simpler, single flow system, only one expansion device 14 is required and the device need only be capable of restricting flow.

In addition, it is only necessary that contaminant indicator 30 or 30' be located in a portion of the refrigerant flow loop where the refrigerant is always in a gaseous state. The location of the contaminant indicator in a bypass line offers an advantage in that indicator bed 31 offers some resistance to refrigerant flow and acts as a filter. Thus increased pumping power would be required to achieve desired refrigerant flow in the system depicted in FIG. 1. And the flow resistance of indicator bed 31 may increase with system total operating time as particles carried in the refrigerant are filtered and collect at the bed's upstream end.

FIGS. 3 and 4, respectively depict an overall pictorial and a sectioned side elevation view of indicator 30'. Casing 34 encloses indicator bed 31, the composition of which will be described below. Casing 34 has transparent wall portion 37, through which indicator bed 31 may be viewed from outside the indicator system refrigerant enters casing 34 through inlet 32, flows through indicator bed 31 and exits through outlet 33.

As refrigerant flows through casing 34 from inlet 32, it first passes through filter 41, then through orifice 51 in flow restrictor 52, then through a first retainer disk 35, then through indicator bed 31, then through a second retainer disk 35 before exiting casing 34 through outlet 33. Retainer disks 35, held in place against indicator bed 31 by springs 36, are porous. The disks serve to keep the granular material of the bed in place and prevent it from leaving casing 34.

Indicator 30, not illustrated except schematically in FIG. 1, could externally appear very similar to indicator 30' but would differ internally in that it would lack filter 41 and flow restrictor 51.

Indicator bed 31 comprises a chemical compound that provides a visual indication, usually by a color change, of the presence of acid in the refrigerant flowing through the bed. The chemical compound may be, depending on the application, one of two types. It may be of a type that undergoes only a temporary change in color in the presence of acid, returning to its original color when the acid is removed from the refrigerant. Another type of compound undergoes a permanent color change regardless of whether the acid is subsequently removed. Both types are useful. The first or regenerative type would find use where the indicator is monitored frequently, or where a technician is monitoring the progress and success of cleanup procedures. The second or permanent type would find use in an application where it is desired to obtain a record of the presence of acid in the system at any time since the last observation of the indicator.

One suitable choice of an acid indicating medium in an indicator bed of the permanent change type is bromophenol blue. This medium can be deposited in a glycerol film on a silica sand base to form indicator bed 31. U.S. Pat. No. 4,923,806 contains a detailed method of making an indicating medium of this regenerative type. Such a bed affords a very large exposure of the bromophenol blue to the refrigerant and any entrained acid while offering little resistance to the refrigerant flow. The indicating medium is normally blue in color but changes to a yellowish color in the presence of acid.

One suitable choice of an acid indicating medium for use in an indicator bed of the regenerative type is meta-cresol purple sodium salt. This can be deposited in a glycerol film on a silica sand base to form indicator bed 31. Such a bed has the same advantages discussed for the meta-cresol purple. The meta-cresol purple sodium salt indicating medium prepared as discussed below is normally a golden color but permanently changes to a pinkish color in the presence of acid.

An acid indicating medium of meta-cresol purple sodium salt is a mixture of three parts meta-cresol purple sodium salt indicator to an amount of glycerine in the range of five to 20 parts (by weight) disposed on a silica sand base. The medium is prepared in the following manner:

1. Dissolve the indicator and glycerine mixture in an amount of a suitable solvent sufficient to make a solution of 300 to 1200 ppm of indicator and 2000 ppm of glycerine.
2. Adjust the color of the dissolved mixture to reddish-orange by adding 0.1 normal HCl (hydrochloric acid).
3. Pour a portion of the mixture on to a bed of silica sand having grains of a suitable size until all of the sand is wetted with the mixture but there is no excess liquid mixture present in the bed.
4. Agitate the liquid mixture and the sand until the mixture has coated all of the sand particles.
5. Slowly heat the mixture of sand and liquid to evaporate the solvent and until the coated sand is dry and free flowing. Do not exceed 70° C. (158° F.) to avoid overheating the mixture. Overheating is indicated by a change in color of the chemical mixture. Drying can be promoted by agitating the coated sand and by purging the container with a gas such as nitrogen or argon that is free of moisture.
6. Remove the container containing the coated sand from the drying apparatus and seal it to isolate it from any sources of moisture.

The meta-cresol purple sodium salt indicating medium should have a dye content of approximately 90 percent (Aldrich No. 21,176-13 or equivalent is suitable). The granular silica sand should be sifted through sieves of 30 and 50 mesh size, retaining the sand that gasses through the 30 mesh sieve and does not pass through the 50 mesh sieve. A 30 mesh sieve will pass grains of 600 microns ($\mu$m) (about 0.0234 inch) or less (a Fisher Scientific No. 04-881-10 P sieve is suitable). A 50 mesh sieve will pass grains of 300 microns ($\mu$m) (about 0.0117 inch) or less (a Fisher Scientific No. 04-881-10 T sieve is suitable).

We claim:

1. An improved vapor compression refrigeration system (10, 10') of the type in which a compressor (11), having a suction (23) and a discharge (22), circulates refrigerant through a closed loop and in which there is a portion of said closed loop where, during operation, said refrigerant is in a gaseous state, the improvement comprising:

an indicator (30, 30') for detecting the presence of acid contamination in said refrigerant located in a bypass line between said suction and said discharge.

2. The refrigeration system of claim 1 in which said indicator contains an indicating bed (31) that changes color if there is acid present in said refrigerant.

3. The refrigeration system of claim 2 in which the change in color of said indicator bed occurs only when there is acid present in the refrigerant passing through said indicator bed and the color of said indicator bed returns to its original color when there no longer acid present in the refrigerant.

4. The refrigeration system of claim 3 in which said indicator bed comprises meta-cresol purple blue in a glycerol film deposited on a silica sand base.

5. The refrigeration system of claim 2 in which the color to which said indicator bed changes in the presence of acid is permanent and remains even if there is no longer acid present in the refrigerant.

6. The refrigeration system of claim 5 in which said indicator bed comprises bromophenol blue sodium salt in a glycerol file deposited on a silica sand base.

7. The refrigeration system of claim 1 in which said indicator has means (37) for viewing said indicating bed from a point external to said indicator.

8. The refrigeration system of claim 7 in which said indicator has a casing (34) and said viewing means comprises a transparent wall portion in said casing.

9. The refrigeration system of claim 1 in which said indicator further comprises an indicator bed that is in downstream refrigerant flow relationship with a flow restrictor (52).

10. The refrigeration system of claim 9 in which said indicator further comprises a filter (41) that is in upstream refrigerant flow relationship with said flow restrictor.

* * * * *